United States Patent [19]

Pence

[11] 4,409,976
[45] Oct. 18, 1983

[54] ANKLE SUPPORT

[76] Inventor: Artie L. Pence, 4141 Conner Dr., Marion, Ind. 46952

[21] Appl. No.: 380,223

[22] Filed: Sep. 20, 1982

Related U.S. Application Data

[63] Continuation of Ser. No. 193,287, Oct. 2, 1980, abandoned.

[51] Int. Cl.$^3$ .............................................. A61F 13/06
[52] U.S. Cl. .................................. 128/166; 128/80 H
[58] Field of Search ............................. 128/166, 80 H

[56] References Cited

U.S. PATENT DOCUMENTS

| | | | |
|---|---|---|---|
| 1,027,897 | 5/1912 | Quenzer | 128/166 |
| 1,084,197 | 1/1914 | Collis | 128/166 |
| 3,515,136 | 6/1970 | Baker | 128/166 |
| 3,674,023 | 7/1972 | Mann | 128/166 |
| 4,133,311 | 1/1979 | Karczewski | 128/80 H X |
| 4,237,874 | 12/1980 | Nelson | 128/80 H |

Primary Examiner—John D. Yasko
Attorney, Agent, or Firm—Gust, Irish, Jeffers & Hoffman

[57] ABSTRACT

An ankle support having a main body portion to extend about the Achilles' tendon of a foot and along the inner and outer sides of that foot with a tongue portion and overlapping first strap portion passing across the ankle to completely encircle the ankle of a wearer and having a stirrup portion depending from the main body portion to pass beneath the arch and sole of the foot leaving the heel and toes exposed is disclosed. The main body portion, first strap portion and tongue are formed as different regions within a single sheet of multi-layer fabric with the stirrup portion being formed from a separate piece of the same multi-layer fabric and joined by stitching to the main body portion in two regions along one edge thereof. A pair of side stiffening members are sandwiched between main body portion layers to reduce sidewise flexing of the ankle joint. Optionally, a second strap portion may be formed integral with and extending from the main body portion adjacent the tongue for tightening the support about an ankle above the region of the first strap portion with the two straps encircling the ankle in opposed senses. The straps are fastened to the main body or tongue portion employing contact fastener material such as Velcro.

3 Claims, 7 Drawing Figures

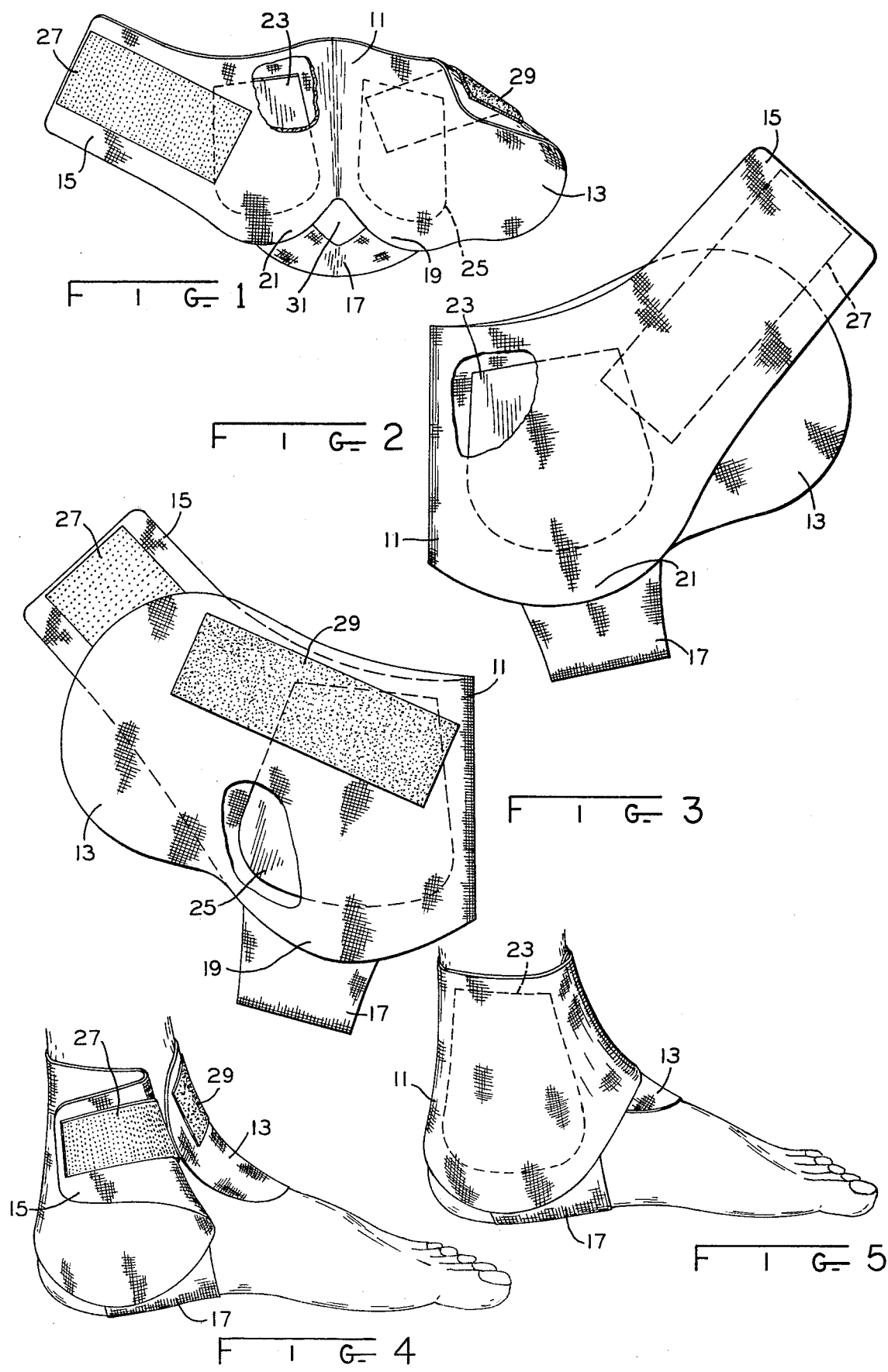

ANKLE SUPPORT

This is a continuation of application Ser. No. 193,287, filed Oct. 2, 1980, now abandoned.

BACKGROUND OF THE INVENTION

Among athletes and non-athletes alike the sprained ankle is one of the most common injuries. A wide variety of supports, braces, elastic bandages and the like have been devised to prevent or reduce the severity of ankle sprains but have met with little success. The non-athlete generally does little or nothing to prevent such sprains, while athletes frequently have their ankles taped by a trainer as a sprain prevention technique, as well as a technique allowing the athlete to perform in spite of a prior injury. This almost universal preventative technique of ankle taping is a relatively costly process both in terms of the trainer time required for the taping process and the material cost. Further, a poorly done ankle taping is almost totally ineffective. Current estimates of the cost to an athletic department are between one dollar and thirty cents and one dollar and fifty cents for each athlete taped.

SUMMARY OF THE INVENTION

Among the several objects of the present invention may be noted the provision of an ankle support which may be easily applied by an inexperienced person, is of moderate cost, and has a long useful life; the provision of an ankle support to reduce the likelihood of a sprained ankle or to reduce the severity in the few cases where a sprain does occur; the provision of an ankle support useful in conjunction with ankle tapings on an already injured individual; and the provision of an ankle support which will reduce sidewise flexing of the ankle joint while allowing substantially unimpeded dorsiflexion thereof. These and other objects and advantageous features of the present invention will be in part apparent and in part pointed out hereinafter.

In general an ankle support has a main body portion for passing around the Achilles' tendon and along the inner and outer sides of the foot with a tongue portion extending from and integral with the main body portion for passing over a portion of the instep of the foot. A first strap portion also integral with and extending from the main body portion is located opposite the tongue portion to lap over the tongue portion and secure the support about the ankle. A stirrup portion depends from the main body portion intermediate the tongue and first strap portion of pass beneath the arch and sole of the foot, preventing upward movement of the main body portion. The main body portion along with the first strap portion and tongue portion are formed from different portions of the same sheet of multi-layer fabric, while the stirrup portion is formed from a separate piece of that same multi-layer fabric and joined to the main body portion in two regions along one edge thereof by stitching. Stiffening members sandwiched between the main body portion layers lie along the inner and outer sides of the ankle. The strap portion attaches to the main body portion by means of a contact fastener material such as Velcro. The support may be made of cloth-backed imitation leather or a canvas-like cloth material, for example, and in an alternate form the strap portion is made somewhat more narrow, and a second strap portion integral with and extending from the main body portion adjacent the tongue portion may also be provided with that second strap encircling the ankle above the region of the first strap portion.

BRIEF DESCRIPTION OF THE DRAWING

FIG. 1 is a perspective view of an open ankle support from the toe end thereof;

FIG. 2 is a right side elevation view of the support of FIG. 1;

FIG. 3 is a left side elevation view of the support of FIG. 1;

FIG. 4 is a view from the right side illustrating the support partially in position about a wearer's ankle;

FIG. 5 illustrates completion of the positioning of FIG. 4;

Corresponding reference characters indicate corresponding parts throughout the several views of the drawing.

Figure 6:
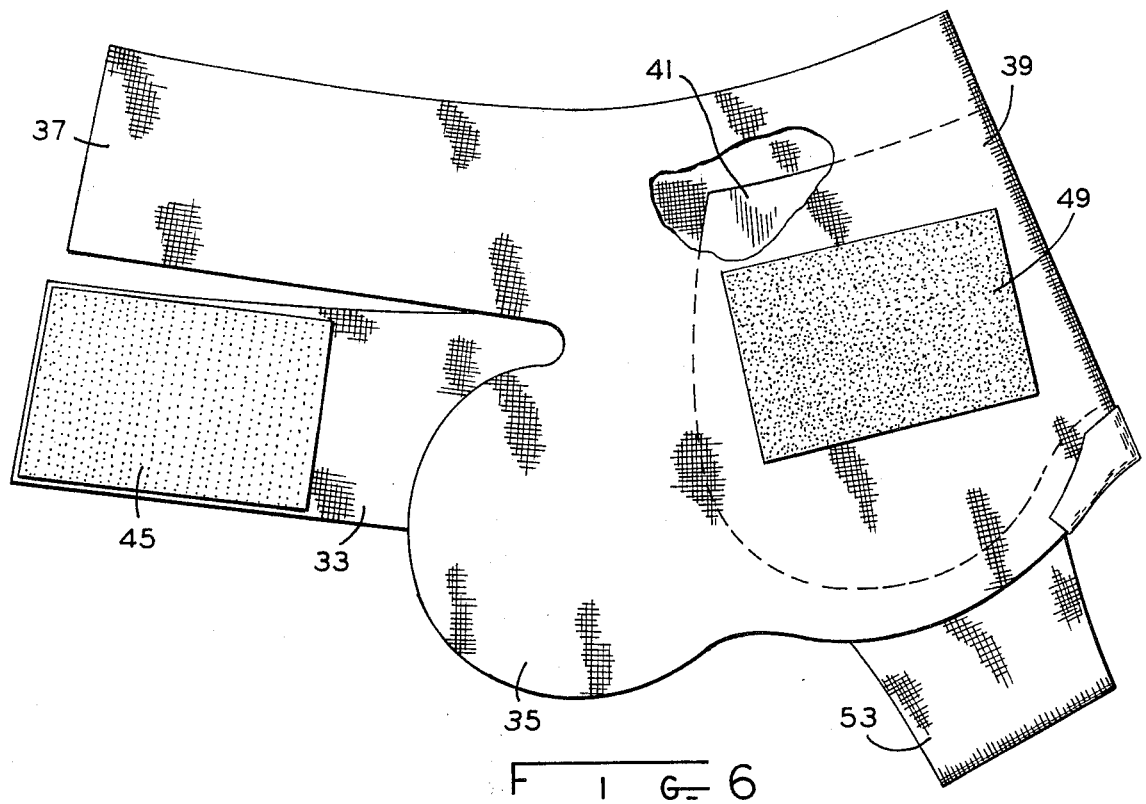
FIG. 6 is a left side elevation view similar to FIG. 3 illustrating a modified form of the ankle support.

The exemplifications set out herein illustrate a preferred embodiment of the invention in one form thereof and such exemplfications are not to be construed as limiting the scope of the disclosure or the scope of the invention in any manner.

DESCRIPTION OF THE PREFERRED EMBODIMENT

Referring first to FIGS. 1 through 3, the ankle support is seen to include a main body portion 11 having a tongue portion 13 integral therewith and extending therefrom in one direction while extending in the other direction and also integral with the main body portion 11 is a first strap portion 15. Depending from the main body portion 11 intermediate the tongue 13 and strap 15 is a stirrup portion 17 which is attached as by stitching along the regions 19 and 21 to the main body portion 11. Directly above the stitched regions 19 and 21 are located two stiffening panels 23 and 25 of, for example, a compressed foam. A single panel extending throughout the support is sometimes preferred. The stiffening panel or panels are sandwiched between the two layers of fabric forming the main body portion as well as the tongue and strap. The stirrup portion 17 may be formed from a separate piece of that same two layer material. The inner surface of strap 15 has stitched thereto a strip 27 of contact fastener material, such as the monofilament hooks of a Velcro fastener, while the outer surface of the main body portion 11 has a strip 29 of contact fastener material, such as a Velcro pad. Pad 29 may extend along either or both the tongue and the main body portion and the strips 27 and 29 provide a great deal of latitude in the foot size to be accommodated.

Figure 7:
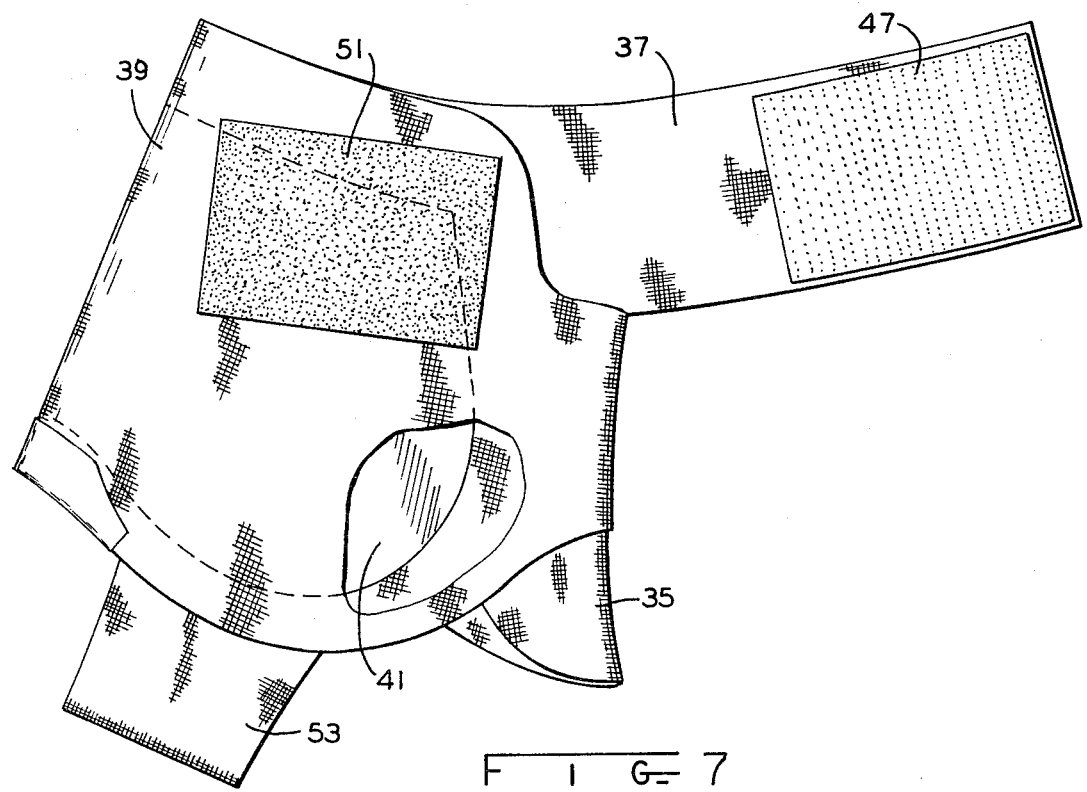
FIG. 7 is a right side elevation view similar to FIG. 2 illustrating the modified ankle support of FIG. 6.

The sheet of multi-layer fabric from which the body, tongue and strap portions are integrally formed may comprise first and second layers of cloth-backed imitation leather, such as Naugahyde superposed and stitched together about the periphery of the sheet, as illustrated in the embodiment of FIGS. 1 through 5, or may, as illustrated in FIGS. 6 and 7, comprise first and second layers of a canvas-like cloth, again superposed and stitched together about the periphery of the sheet. In either case, the support is free of elastic material, and the stirrup ends are typically inserted between the layers prior to stitching, as are the stiffeners 23 and 25.

In use, the user seats his heel firmly in the pocket about opening 31 formed between the back of the body portion and stirrup 17 and thereafter folds tongue 13 firmly over his instep, as illustrated in FIG. 4, and then laps the strap 15 over the tongue portion, joining those two portions by the contact fastener material, as illustrated in FIG. 5. The user may, for comfort, prefer to wear a sock underneath the support and in most cases will wear a shoe over the support with tight lacing of the shoe helping to minimize lateral slippage of the stirrup 17 beneath the foot.

Certain variations are illustrated in FIGS. 6 and 7 it being understood that these features may be freely chosen and interchanged between the illustrated versions of the support. The support of FIGS. 6 and 7 has strap 33 somewhat more narrow than the analagous strap 15 of FIGS. 1 through 5, and also has tongue portion 35 somewhat smaller than the analagous tongue portion 13 of FIGS. 1 through 3. A second strap portion 37 is formed integral with and extending from the main body portion 39 adjacent tongue portion 35 for tightening the support about an ankle above the region of the first strap portion 33. A pair of stiffening side panels or a single stiffening panel 41 may, as before, be sandwiched between the main body portion layers to lie along the inner and outer sides of the ankle to reduce sidewise flexing of the ankle joint while allowing substantially unimpeded dorsiflexion thereof.

Regions of contact fastener material, such as Velcro hooks 45 and 47, are attached to the inner surfaces of the first strap portion 33 and the second strap portion 37, with mating regions of contact fastener material, such as Velcro pads 49 and 51, on the outer surfaces of main body portion 39 so that the support may be adjustably tightened about any one of a range of sizes of foot. The one mating region of contact fastener material 51 overlies approximately the upper third of the stiffening side panel 43 while the other mating region of contact fastener material 49 overlies approximately the middle third of the other stiffening side panel so that when the support is properly positioned about an ankle, the first and second straps encircle the ankle to opposed senses with the second strap 37 lying above the first strap 45.

As in the embodiment of FIGS. 1 through 5, the stiffening side panel 41 may be about one-sixteenth inch thick to one-eighth inch thick compressed foam of a firmness about sixteen to eighteen. This firmness figure reflects the fact that the reticulated polyester polyurethane open pore foam from which the compressed foam is formed under heat was about sixteen to eighteen times as thick. Suitable materials are marketed under the Trademarks Scottfelt, as well as Ensolite by Uni-Royal. The latter material allows a heat laminating process to replace much of the illustrated stitching. Also as in the first version the stirrup portion 53 may be formed from the same multi-layer material with the ends thereof positioned between layers of the main body portion 39 prior to edge stitching thereof.

From the foregoing it is now apparent that a novel ankle support has been disclosed meeting the objects and advantageous features set out hereinbefore as well as others and that modifications as to the precise configurations, shapes and details may be made by those having ordinary skill in the art without departing from the spirit of the invention or the scope thereof as set out by the claims which follow.

What is claimed is:
1. An elastic-free ankle support to extend about the Achilles' tendon of a foot along the inner and outer sides of the foot and across the ankle to completely encircle the ankle of a wearer and to pass beneath the arch and sole of the foot while leaving the toes exposed comprising:
   a main body portion for passing around the Achilles' tendon including side portions thereof for passing along the inner and outer sides, respectively, of the foot,
   a tongue portion extending from one side of the main body portion for passing from the instep over the front of the foot,
   a first strap portion extending from the main body portion side opposite the tongue portion to lap over the tongue portion and secure the support to the ankle, said first strap being substantially non-elastic and non-elastically connected to the side of the main body portion opposite the tongue portion, said first strap being narrower than said tongue,
   a second non-elastic strap portion non-elastically connected to and extending from the same side of the main body portion as the tongue portion and being adjacent thereto,
   a stirrup portion depending from the main body portion intermediate the tongue and first strap portions to pass beneath the arch and sole of the foot to prevent upward movement of the main body portion,
   a region of contact fastener material on an inner surface of the first strap portion and a mating region of contact fastener material on an outer surface of the main body portion side from which the tongue extends whereby the support first strap portion may be adjustably tightened about any one of a range of sizes of foot,
   a second region of contact fastener material on an inner surface of the second strap portion and a mating region of contact fastener material on the side of the main body portion from which the first strap portion extends whereby the support second strap portion may be adjustably tightened about any one of the range of sizes of foot,
   said first mentioned mating region of contact fastener material being positioned relative to the second strap and the second region of contact fastener material being positioned relative to the first strap to position the second strap above the first strap with the straps encircling the ankle in opposed senses and pulling the side portions of the main body portion in opposite directions when the support is properly positioned about an ankle and the straps are tightened, and
   stiffening panels in the side portions of the main body portion.
2. The ankle support of claim 1 wherein one mating region of contact fastener material overlies approximately the upper third of one stiffening side panel while the other mating region of contact fastener material overlies approximately the middle third of the other stiffening side panel.
3. The ankle support of claim 1 wherein each stiffening side panel is formed of a compressed foam.

* * * * *